(12) United States Patent
Koster et al.

(10) Patent No.: US 8,017,824 B2
(45) Date of Patent: Sep. 13, 2011

(54) HYDROCARBON CONVERSION PROCESSES USING UZM-29 AND UZM-29HS CRYSTALLINE ZEOLITIC COMPOSITIONS

(75) Inventors: Susan C. Koster, Carpentersville, IL (US); Jaime G. Moscoso, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 161 days.

(21) Appl. No.: 12/535,248

(22) Filed: Aug. 4, 2009

(65) Prior Publication Data

US 2011/0034746 A1 Feb. 10, 2011

(51) Int. Cl.
*C07C 5/27* (2006.01)
*C07C 2/66* (2006.01)
*C07C 2/54* (2006.01)
*C07C 1/207* (2006.01)

(52) U.S. Cl. ........ 585/739; 585/640; 585/639; 585/467; 585/722

(58) Field of Classification Search ............ 585/739, 585/640, 639, 467, 722
See application file for complete search history.

(56) References Cited

U.S. PATENT DOCUMENTS

| | | | |
|---|---|---|---|
| 4,310,440 A | 1/1982 | Wilson et al. | |
| 4,440,871 A | 4/1984 | Lok et al. | |
| 5,157,196 A | 10/1992 | Crossland et al. | |
| 5,157,197 A | 10/1992 | Cooper et al. | |
| 6,776,975 B2 | 8/2004 | Wilson et al. | |
| 2005/0095195 A1 | 5/2005 | Lewis et al. | |

OTHER PUBLICATIONS

U.S. Appl. No. 12/535,254, filed Aug. 4, 2009, Koster et al.
Cichocki, Andrzej, Method of obtaining phyllipzite-type zeolite exhibiting properties of a molecular sieve, PN 162653B1 (1993) (English Abstract Only).
Barrett et al., A new addition to the Phillipsite family of molecular sieves: A divalent metal-iron-framework . . . , Solid State Sciences 8 (2006) 337-341.
Chen et al., The Synthesis of Phillipsite, National Taiwan Univ., Western Pacific Earth Sciences, vol. 2, No. 4, p. 381-392, Figs, 4 Tabs. Taipei, Taiwan, Nov. 2002.
Gualtieri, A.F., Study of NH4+ in the zeolite phillipsite by combined synchrotron powder diffraction and IR spectroscopy, Acta Cryst., (2000) B56, 584-593.

*Primary Examiner* — Thuan Dinh Dang
(74) *Attorney, Agent, or Firm* — Frank S Molinaro

(57) ABSTRACT

This invention relates to hydrocarbon conversion processes using UZM-29 and UZM-29HS zeolitic compositions. The UZM-29 zeolites are represented by the empirical formula:

$$M_m^{n+}R^+_r Al_{1-x}E_x Si_y O_z$$

UZM-29 has the PHI structure type topology but is thermally stable up to a temperature of at least 350° C. UZM-29HS is a high silica version of UZM-29 and is represented by the empirical formula: $M1^{m+}_a Al_{(1-x)}E_x Si_y O_z$. Examples of the hydrocarbon conversion processes are isomerization of alkanes, especially butane and the conversion of oxygenates to olefins.

4 Claims, No Drawings

HYDROCARBON CONVERSION PROCESSES USING UZM-29 AND UZM-29HS CRYSTALLINE ZEOLITIC COMPOSITIONS

FIELD OF THE INVENTION

This invention relates to hydrocarbon conversion processes using a new family of crystalline zeolitic compositions designated UZM-29. UZM-29 has the empirical formula of:

$$M_m^{n+}R_r^+Al_{1-x}E_xSi_yO_z$$

UZM-29 has a similar topology to phillipsite (PHI structure type) but has characteristics which differentiate it from phillipsite and phillipsite analogs. UZM-29HS is a high silica version of UZM-29.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

Applicants have successfully prepared a new family of crystalline aluminosilicate compositions designated UZM-29. UZM-29 has a three dimensional framework structure with the topology of phillipsite zeolite or the PHI structure type. UZM-29 is prepared using a combination of two organic structure directing agents such as pentaethonium ammonium dihydroxide, [HEPDA(OH)$_2$] and ethyltrimethyammonioum hydroxide (ETMAOH) plus an alkali metal such as sodium using the Charge Density Mismatch Process for synthesizing zeolites as described in US Patent Application Publication No. 2005/0095195. UZM-29HS is synthesized from UZM-29 by various methods where aluminum is removed from the framework and replaced with silicon.

SUMMARY OF THE INVENTION

As stated, the present invention relates to hydrocarbon conversion processes using UZM-29 and UZM-29HS. Accordingly, one embodiment of the invention is a hydrocarbon conversion process comprising contacting a hydrocarbon stream with a catalyst at hydrocarbon conversion conditions to give a converted product, the catalyst comprising a macroporous crystalline zeolite selected from the group consisting of UZM-29, UZM-29HS and mixtures thereof, where UZM-29 has a three-dimensional framework of at least $AlO_2$ and $SiO_2$ tetrahedral units and an empirical composition in the as synthesized and anhydrous basis expressed by an empirical formula of:

$$M_m^{n+}R_r^+Al_{1-x}E_xSi_yO_z$$

Where M is at least one exchangeable cation selected from the group consisting of alkali and alkaline earth metals, "m" is the mole ratio of M to (Al+E) and varies from greater than zero to about 2.0, R is a singly or doubly charged organoammonium cation selected from the group of pentaethonium ammonium, ethyltrimethylammonium (ETMA$^+$), hexamethonium ammonium, diquat-4, pentyltrimethylammonium, choline, diethyldimethyl ammonium (DEDMA$^+$), trimethylpropylammonium, dimethyldiethanolammonium, tetraethyl ammonium (TEA$^+$), tetrapropylammonium (TPA$^+$), dimethylhexylamine, diethanolamine, and mixtures thereof, "r" is the mole ratio of R to (Al+E) and has a value of about 0.25 to about 2.0, "n" is the weighted average valence of M and has a value of about 1 to about 3, E is an element selected from the group consisting of gallium, iron, boron, and mixtures thereof, "x" is the mole fraction of E and has a value from 0 to about 1.0, "y" is the mole ratio of Si to (Al+E) and varies from greater than 2 to about 10 and "z" is the mole ratio of O to (Al+E) and has a value determined by the equation:

$$z=(m \cdot n+p \cdot r+3+4 \cdot y)/2$$

and is characterized in that it has the x-ray diffraction pattern having at least the d-spacings and intensities set forth in Table A:

TABLE A

| 2Θ | d(Å) | I/Io % |
|---|---|---|
| 10.74-10.86 | 8.14-8.23 | w-m |
| 12.50-12.6 | 6.99-7.07 | vs |
| 16.60-16.72 | 5.30-5.33 | s-vs |
| 17.48-17.7 | 5.01-5.07 | m |
| 17.80-17.88 | 4.96-4.98 | w |
| 20.74-20.81 | 4.26-4.28 | w |
| 21.74-21.94 | 4.05-4.08 | m-s |
| 22.82-22.88 | 3.88-3.89 | w-m |
| 24.40-24.52 | 3.62-3.64 | w |
| 25.08-25.10 | 3.54-3.55 | w |
| 26.06-26.1 | 3.41-3.42 | w-m |
| 27.10-27.12 | 3.28-3.29 | m |
| 27.70-27.90 | 3.20-3.22 | m |
| 28.26-28.44 | 3.14-3.15 | s-vs |
| 30.00-30.30 | 2.94-2.97 | m |
| 32.58-32.64 | 2.74-2.75 | w |
| 33.02-33.03 | 2.71-2.71 | w |
| 33.28-33.29 | 2.69-2.70 | m |
| 33.76-33.82 | 2.65-2.65 | w |
| 37.481-37.56 | 2.39-2.40 | w |
| 41.202-42.41 | 2.13-2.19 | w |
| 45.96-46.01 | 1.97-1.98 | w |
| 51.4-52.00 | 1.70-1.77 | w |
| 54.05-54.26 | 1.69-1.70 | w | and is thermally stable up to a temperature of at least 400° C.; and UZM-29HS has a three-dimensional framework of at least $AlO_2$ and $SiO_2$ tetrahedral units and an empirical composition on an anhydrous basis of:

$$M1_a^{m+}Al_{(1-x)}E_xSi_yO_z$$

Where M1 is at least one exchangeable cation selected from the group consisting of alkali and alkaline earth metals, rare earth metals, ammonium ion, hydrogen ion and mixtures thereof, "a" is the mole ratio of M1 to (Al+E) and varies from about 0.05 to about 50, "n" is the weighted average valence of M1 and had a value of about +1 to about +3, E is an element selected from the group consisting of gallium, iron, boron and mixtures thereof, "x" is the mole fraction of E and varies from 0 to 1.0, y' is the mole ratio of Si to (Al+E) and varies from greater than about 4 to virtually pure silica and z' is the mole ratio of O to (Al+E) and has a value determined by the equation:

$$z'=(a\cdot n+3+4\cdot y')/2$$

the zeolite characterized in that it has an x-ray diffraction pattern having at least the d=spacings and relative intensities set forth in Table C:

TABLE C

| 2Θ    | d(Å) | I/Io % |
|-------|------|--------|
| 10.86 | 8.14 | m      |
| 12.66 | 6.99 | vs     |
| 16.72 | 5.30 | m      |
| 17.70 | 5.01 | m      |
| 20.74 | 4.28 | w      |
| 21.94 | 4.05 | m      |
| 22.82 | 3.89 | w      |
| 24.52 | 3.63 | w      |
| 25.04 | 3.55 | w      |
| 26.06 | 3.42 | w      |
| 27.62 | 3.23 | w      |
| 27.70 | 3.22 | m      |
| 28.44 | 3.14 | m      |
| 30.30 | 2.95 | m      |
| 33.03 | 2.71 | w      |
| 33.76 | 2.65 | w      |
| 36.31 | 2.47 | w      |
| 37.48 | 2.40 | w      |
| 37.86 | 2.37 | w      |
| 40.96 | 2.20 | w      |
| 41.33 | 2.18 | w      |
| 42.41 | 2.13 | w      |
| 52.00 | 1.76 | w      |
| 53.86 | 1.70 | w      |
| 54.06 | 1.69 | w      |

And is thermally stable up to a temperature of at least 400° C.

These and other objects and embodiments of the invention will become more apparent after the detailed description of the invention.

DETAILED DESCRIPTION OF THE INVENTION

As stated, the present invention relates to hydrocarbon processes using two new families of zeolitic compositions. Applicants have prepared a new family of macroporous crystalline zeolites having a three dimensional structure of at least $SiO_2$ tetrahedral units designated the UZM-29 family of zeolites which has the topological structure related to PHI as described in *Atlas of Zeolites Framework Types*, which is maintained by the International Zeolite Association Structure Commission at http://topaz.ethz.ch/IZA-SC/StdAtlas.htm. The UZM-29 has an empirical composition in the as-synthesized form and on an anhydrous basis expressed by the empirical formula:

where M is at least one exchangeable cation and is selected from the group consisting of alkali metal ions, alkaline earth metal ions, and rare earth metal ions. Specific examples of the M cations include but are not limited to lithium, sodium, potassium, rubidium, cesium, calcium, strontium, barium, lanthanum, ytterbium and mixtures thereof, with Na being preferred. R is an organoammonium cation or an amine, examples of which include but are not limited to the pentaethonium ammonium (HEPDA)$^{-2}$, ethyltrimethylammonium, diquat-4, choline cation $[(CH_3)_3NCH_2CH_2OH]^+$, diethyldimethylammonium, hexamethonium ammonium, trimethylpropylammonium, trimethylpentylammonium, dimethyldiethanolammonium, tetraethylammonium (TEA$^+$), tetrapropylammonium TPA$^+$, dimethylbutylamine, diethanolamine and mixtures there of and "r" is the mole ratio of R to (Al+E) and varies from about 0.25 to about 2.0. Pentaethonium ammonium (HEPDA)$^{+2}$ is a preferred organoammonium cation. The value of "p" which is the weighted average valence of R varies from 1 to about 2. The value of "n" which is the weighted average valence of M varies from about 1 to about 3 while "m" is the mole ratio of M to (Al+E) and varies from greater than zero to about 2. The ratio of silicon to (Al+E) is represented by "y" which varies from greater than 2 to about 10. E is an element which is tetrahedrally coordinated, is present in the framework and is selected from the group consisting of gallium, iron and boron. The mole fraction of E is represented by "x" and has a value from 0 to about 1.0, while "z" is the mole ratio of O to (Al+E) and is given by the equation:

$$z=(m\cdot n+p\cdot r+3+4\cdot y)/2.$$

When M is only one metal, then the weighted average valence is the valence of that one metal, i.e. +1 or +2.

However, when more than one M metal is present, the total amount of:

$$M_m^{n+}=M_{m1}^{(n1)+}+M_{m2}^{(n2)+}+M_{m3}^{(n3)+}+\ldots$$

and the weighted average valence "n" is given by the equation:

$$n=\frac{m_1\cdot n_1+m_2\cdot n_2+m_3\cdot n_3+\ldots}{m_1+m_2+m_3\ldots}$$

When more than one organoammonium cation is present, the total amount of:

$$R_r^{p+}=R_{r1}^{(p1)+}+R_{r2}^{(p2)+}+R_{r3}^{(p3)+}+\ldots$$

And the weighted average valence "p" is given by the equation:

$$p=\frac{r_1\cdot p_1+r_2\cdot p_2+r_3\cdot p_3+\ldots}{r_1+r_2+r_3\ldots}$$

UZM-29 is prepared by a hydrothermal crystallization of a reaction mixture prepared by combining reactive sources of M, R, aluminum, silicon and optionally E. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica and alkali silicates. Sources of the E elements include but are not limited to alkali borates, boric acid, precipitated gallium oxyhydroxide, gallium sulfate, ferric sulfate, and ferric chloride. Sources of the M metals include the halide salts, nitrate salts, acetate salts, and hydroxides of the respective alkali, alkaline earth, or rare earth metals. R is an organoammonium cation or an amine selected from the group consisting of pentaethonium ammonium (HEPDA)$^{+2}$, ethyltrimethylammonium, hexamethonium ammonium, diquat-4, trimethylpentylammonium, choline, diethyldimethylammonium, TEA, TPA, trimethylpropylammonium, dimethyldiethanolammonium, dimethylbutylamine, diethanolamine and mixtures thereof, and the sources include the hydroxide, chloride, bromide, iodide and fluoride compounds. Specific examples include without limitation pentaethonium ammonium dihydroxide and, ethyltrimethylammonium hydroxide. The reaction mixture containing reactive sources of the desired components can be described in terms of molar ratios of the oxides by the formula:

$$aM_{2/n}O:bR_{2/p}O:1-cAl_2O_3:cE_2O_3:dSiO_2:eH_2O$$

where "a" varies from greater than 0 to about 5.0, "b" varies from about 1.5 to about 120, "c" varies from 0 to 1.0, "d" varies from about 2 to about 20, and "e" varies from about 2.5 to about 4000. If alkoxides are used, it is preferred to include a distillation or evaporative step to remove the alcohol hydrolysis products. The reaction mixture is now reacted at a temperature of about 100° C. to about 200° C. and preferably from about 125° C. to about 175° C. for a period of about 1 day to about 3 weeks and preferably for a time of about 3 days to about 10 days in a sealed reaction vessel under autogenous pressure. After crystallization is complete, the solid product is isolated from the reaction mixture by means such as filtration or centrifugation, and then washed with deionized water and dried in air at ambient temperature up to about 100° C.

A preferred synthetic approach to make UZM-29 utilizes the Charge Density Mismatch process disclosed in US Patent Application Publication No. US 2005/0095195 which is incorporated by reference in its entirety. The charge density mismatch process allows multiple structure directing agents to cooperate to crystallize a single structure. The method employs appropriate quaternary ammonium hydroxides to solubilize aluminosilicate species, creating a reaction mixture which has difficulty crystallizing and condensing to form a solid under synthesis conditions. These preformed aluminosilicate species require crystallization-inducing agents such as alkali and alkaline earth metals and more highly charged organoammonium cations that are separately introduced and cooperate with the quaternary ammonium template to affect the crystallization process. A preferred combination for the synthesis of UZM-29 is pentaethonium ammonium (HEPDA)$^{-2}$ dihydroxide as the charge density mismatch template and sodium as the crystallization inducing agent.

The UZM-29 crystalline microporous zeolite having at least SiO$_2$ tetrahedral units, which is obtained from the above-described process, is characterized by an x-ray diffraction pattern having at least the d-spacings and relative intensities set forth in Table A below.

TABLE A

| 2Θ | d(Å) | I/Io % |
|---|---|---|
| 10.74-10.86 | 8.14-8.23 | w-m |
| 12.50-12.6 | 6.99-7.07 | vs |
| 16.60-16.72 | 5.30-5.33 | s-vs |
| 17.48-17.7 | 5.01-5.07 | m |
| 17.80-17.88 | 4.96-4.98 | w |
| 20.74-20.81 | 4.26-4.28 | w |
| 21.74-21.94 | 4.05-4.08 | m-s |
| 22.82-22.88 | 3.88-3.89 | w-m |
| 24.40-24.52 | 3.62-3.64 | w |
| 25.08-25.10 | 3.54-3.55 | w |
| 26.06-26.1 | 3.41-3.42 | w-m |
| 27.10-27.12 | 3.28-3.29 | m |
| 27.70-27.90 | 3.20-3.22 | m |
| 28.26-28.44 | 3.14-3.15 | s-vs |
| 30.00-30.30 | 2.94-2.97 | m |
| 32.58-32.64 | 2.74-2.75 | w |
| 33.02-33.03 | 2.71-2.71 | w |
| 33.28-33.29 | 2.69-2.70 | m |
| 33.76-33.82 | 2.65-2.65 | w |
| 37.481-37.56 | 2.39-2.40 | w |
| 41.202-42.41 | 2.13-2.19 | w |

TABLE A-continued

| 2Θ | d(Å) | I/Io % |
|---|---|---|
| 45.96-46.01 | 1.97-1.98 | w |
| 51.4-52.00 | 1.70-1.77 | w |
| 54.05-54.26 | 1.69-1.70 | w |

The microporous UZM-29 composition will contain some of the exchangeable or charge balancing cations in its pores. These exchangeable cations can be exchanged for other cations. The UZM-29 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4 in U.S. Pat. No. 6,776,975 B1 which is incorporated by reference in its entirety. Properties that can be modified include porosity, adsorption, Si/Al ratio, acidity, thermal stability, etc.

The UZM-29 composition which is modified by one or more techniques described in the '975 patent (herein UZM-29HS) is described by the empirical formula on an anhydrous basis of:

$$M1'^{n+}_{a'}Al_{(1-x)}E_xSi_{y'}O_{z''}$$

where M1' is at least one exchangeable cation selected from the group consisting of alkali, alkaline earth metals, transitions metals, rare earth metals, ammonium ion, hydrogen ion and mixtures thereof, "a" is the mole ratio of M1' to (Al+E) and varies from greater than 0 to about 2, "n" is the weighted average valence of M1' and has a value of about +1 to about +3, E is an element selected from the group consisting of gallium, iron, boron, and mixtures thereof, "x" is the mole fraction of E and varies from 0 to 1.0, y' is the mole ratio of Si to (Al+E) and varies from greater than 3 to virtually pure silica and z' is the mole ratio of O to (Al+E) and has a value determined by the equation:

$$z'=(a \cdot n+3+4 \cdot y')/2$$

By virtually pure silica is meant that virtually all the aluminum and/or the E metals have been removed from the framework. It is well know that it is virtually impossible to remove all the aluminum and/or E metal. Numerically, a zeolite is virtually pure silica when y' has a value of at least 3,000, preferably 10,000 and most preferably 20,000. Thus, ranges for y' are from 15 to 3,000 preferably greater than 30 to about 3,000; 15 to 10,000 preferably greater than 30 to about 10,000 and 15 to 20,000 preferably greater than 30 to about 20,000.

In specifying the proportions of the zeolite starting composition or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The crystalline UZM-29 zeolite of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species. Specifically, the molecular sieves can be used to separate propane from propylene.

The UZM-29 zeolite of this invention can also be used as a catalyst or catalyst support in various hydrocarbon conversion processes. Hydrocarbon conversion processes are well known in the art and include cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanation and syngas shift process. Specific reaction conditions and the types of feeds which can be used in these processes are set forth in U.S. Pat. Nos. 4,310,440 and 4,440,871, which are incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of 400° to 1200° F. (204-649° C.), preferably between 600° and 950° F. (316-510° C.). Reaction pressures are in the range of atmospheric to about 3,500 psig (24,132 kPa g), preferably between 200 and 3000 psig (1379-20,685 kPa g). Contact times usually correspond to liquid hourly space velocities (LHSV) in the range of about 0.1 $hr^{-1}$ to 15 $hr^{-1}$, preferably between about 0.2 and 3 $hr^{-1}$. Hydrogen circulation rates are in the range of 1,000 to 50,000 standard cubic feet (scf) per barrel of charge (178-8,888 std. $m^3/m^3$), preferably between 2,000 and 30,000 scf per barrel of charge (355-5,333 std. $m^3/m^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the UZM-29 composition using feedstocks such as gas oils, heavy naphthas, deasphalted crude oil residua, etc. with gasoline being the principal desired product. Temperature conditions of 850° to 1100° F., LHSV values of 0.5 to 10 and pressure conditions of from about 0 to 50 psig are suitable.

Alkylation of aromatics usually involves reacting an aromatic ($C_2$ to $C_{12}$), especially benzene, with a monoolefin to produce a linear alkyl substituted aromatic. The process is carried out at an aromatic:olefin (e.g., benzene:olefin) ratio of between 5:1 and 30:1, a LHSV of about 0.3 to about 6 $hr^{-1}$, a temperature of about 100° to about 250° C. and pressures of about 200 to about 1000 psig. Further details on apparatus may be found in U.S. Pat. No. 4,870,222 which is incorporated by reference.

Alkylation of isoparaffins with olefins to produce alkylates suitable as motor fuel components is carried out at temperatures of −30° to 40° C., pressures from about atmospheric to about 6,894 kPa (1,000 psig) and a weight hourly space velocity (WHSV) of 0.1 to about 120. Details on paraffin alkylation may be found in U.S. Pat. Nos. 5,157,196 and 5,157,197, which are incorporated by reference.

Another hydrocarbon conversion process including within this invention is the conversion of oxygenates to olefins and specifically the conversion of methanol to ethylene and propylene. The conversion of methanol to light olefins is effected by contacting the methanol with the UZM-29 or UZM-29HS catalyst at conversion conditions, thereby forming the desired light olefins. The methanol can be in the liquid or vapor phase with the vapor phase being preferred. Contacting the methanol with the UZM-29 or UZM-29HS catalyst can be done in a continuous mode or a batch mode with a continuous mode being preferred. The amount of time that the methanol is in contact with the UZM-29 or UZM-29HS catalyst must be sufficient to convert the methanol to the desired light olefin products. When the process is carried out in a batch process, the contact time varies from about 0.001 hr. to about 1 hr. and preferably from about 0.01 hr. to about 1.0 hr. The longer contact times are used at lower temperatures while shorter times are used at higher temperatures. Further, when the process is carried out in a continuous mode, the Weight Hourly Space Velocity (WHSV) based on methanol can vary from about 1 $hr^{-1}$ to about 1000 $hr^{-1}$ and preferably from about 1 $hr^{-1}$ to about 100 $hr^{-1}$.

Generally, the process must be carried out at elevated temperatures in order to form light olefins at a fast enough rate. Thus, the process should be carried out at a temperature of about 300° C. to about 600° C., preferably from about 400° C. to about 550° C. and most preferably from about 450° C. to about 525° C. The process may be carried out over a wide range of pressure including autogenous pressure. Thus, the pressure can vary from about 0 kPa (0 psig) to about 1724 kPa (250 psig) and preferably from about 34 kPa (5 psig) to about 345 kPa (50 psig).

Optionally, the methanol feedstock may be diluted with an inert diluent in order to more efficiently convert the methanol to olefins. Examples of the diluents which may be used are helium, argon, nitrogen, carbon monoxide, carbon dioxide, hydrogen, steam, paraffinic hydrocarbons, e.g., methane, aromatic hydrocarbons, e.g., benzene, toluene and mixtures thereof. The amount of diluent used can vary considerably and is usually from about 5 to about 90 mole percent of the feedstock and preferably from about 25 to about 75 mole percent.

The actual configuration of the reaction zone may be any well known catalyst reaction apparatus known in the art. Thus, a single reaction zone or a number of zones arranged in series or parallel may be used. In such reaction zones the methanol feedstock is flowed through a bed containing the UZM-29 or UZM-29HS catalyst. When multiple reaction zones are used, one or more UZM-29 or UZM-29HS catalyst may be used in series to produce the desired product mixture. Instead of a fixed bed, a dynamic bed system, e.g., fluidized or moving, may be used. Such a dynamic system would facilitate any regeneration of the UZM-29 or UZM-29HS catalyst that may be required. If regeneration is required, the ELAPO catalyst can be continuously introduced as a moving bed to a regeneration zone where it can be regenerated by means such as oxidation in an oxygen containing atmosphere to remove carbonaceous materials.

References which describe specific process configurations for oxygenate to olefin processes include without limitation U.S. Pat. Nos. 5,714,662 and 6,872,867 B1 both of which are incorporated by reference in their entirety.

The following examples are presented in illustration of this invention and are not intended as undue limitations on the generally broad scope of the invention as set out in the appended claims.

The structures of the UZM-29 family of zeolite compositions of this invention were determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 70° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline compositions from each other and from the compositions of the prior art. In some of the x-ray patterns reported, the relative intensities of the d-spacings are indicated by the notations vs, s, m, and w which represent very strong, strong, medium, and weak, respectively. In terms of 100×I/$I_o$, the above designations are defined as:

w=0-15; m=15-60: s=60-80 and vs=80-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present. Finally, some peaks are identified with special identifiers as follows: very broad (vbr); broad (br); and shoulder (sh).

In order to more fully illustrate the invention, the following examples are set forth. It is to be understood that the examples are only by way of illustration and are not intended as an undue limitation on the broad scope of the invention as set forth in the appended claims.

EXAMPLE 1

An aluminosilicate reaction solution was prepared by mixing in a container 45.59 g of aluminum sec-butoxide and 534.58 g pentaethonium ammonium hydroxide, and 132.30 g ethyltrimethyammonioum hydroxide (20% solution), while stirring vigorously. After thorough mixing, 125.95 g of Ludox™ AS-40 (SiO$_2$, 40%) were added. The reaction mixture was homogenized for 30 minutes, sealed in a Teflon™ bottle and placed in an oven and the mixture reacted for about 18 hours at 100° C. Analysis showed the resultant aluminosilicate solution had a Si/Al=4.87.

EXAMPLE 1A

In one container 4.02 g of NaCl were dissolved in 15 g of deionized water. The NaCl solution was slowly added to 150 grams of the aluminosilicate solution from Example 1 and stirred for 30 minutes. The gel was placed in 45-mL Parr reactors and the reaction mixtures reacted at 150° C. for 288 hours. The solid product was recovered by centrifugation, washed with de-ionized water and dried at 100° C. The product was identified as UZM-29 by x-ray diffraction. Representative diffraction lines for the product are shown in Table 1. Elemental analysis showed that the UZM-29 product had a Si/Al=4.09; Na/Al=0.66. This material was still crystalline after calcination at 500° C. for 2 hours in air.

Scanning Electron Microscopy (SEM) showed spherical crystal aggregates that contained long prismatic crystals in each aggregate.

TABLE 1

| 2Θ | d(Å) | I/Io % |
|---|---|---|
| 10.74 | 8.23 | m |
| 12.58 | 7.03 | vs |
| 16.64 | 5.32 | vs |
| 17.48 | 5.07 | m |
| 17.88 | 4.96 | w |
| 20.81 | 4.27 | w |
| 21.82 | 4.07 | s |
| 22.90 | 3.88 | m |
| 24.48 | 3.63 | w |
| 26.10 | 3.41 | m |
| 27.10 | 3.29 | m |
| 27.86 | 3.20 | m |
| 28.44 | 3.14 | s |
| 30.00 | 2.98 | m |
| 32.64 | 2.74 | w |
| 33.02 | 2.71 | w |
| 33.28 | 2.69 | m |
| 33.82 | 2.26 | w |
| 37.56 | 2.39 | w |
| 41.20 | 2.19 | w |
| 46.00 | 1.97 | w |
| 51.45 | 1.77 | w |
| 54.18 | 1.69 | w |

EXAMPLE 2

An aluminosilicate reaction solution was prepared by mixing in a container 72.77 g of aluminum sec-butoxide and 761.18 g of pentaethonium ammonium hydroxide, and 150.70 g of ethyltrimethyammonioum hydroxide (20% solution), while stirring vigorously. After thorough mixing, 215.31 g of Ludox™ AS-40 (SiO$_2$, 40%) was added. The reaction mixture was homogenized for 30 minutes, sealed in a Teflon™ bottle and placed in an oven for 18 hours at 100° C. to react the mixture and then cooled to provide an aluminosilicate solution.

In one container 11.87 g of NaOH were dissolved in 100 g of deionized water and in another container 8.73 g of NaCl was dissolved in 86 g of deionized water. Both solutions were slowly added to the aluminosilicate solution and stirred for 30 minutes. The resultant gel was added to a 2-liter reactor and the mixture reacted at 150° C. for 45 hours. The solid product was recovered by centrifugation, washed with de-ionized water and dried at 100° C. The product was identified as UZM-29 by x-ray diffraction. Representative diffraction lines for the product are presented in Table 2. Elemental analysis showed that the UZM-29 product had a Si/Al=3.26; Na/Al=0.74, N/Al=0.23

Scanning Electron Microscopy (SEM) showed spherical crystal aggregates that contained long prismatic crystals in each aggregate.

TABLE 2

| 2Θ | d(Å) | I/Io % |
|---|---|---|
| 10.78 | 8.20 | w |
| 12.56 | 7.04 | vs |
| 16.64 | 5.32 | s |
| 17.50 | 5.06 | m |
| 17.80 | 4.98 | w |
| 21.74 | 4.08 | m |
| 22.88 | 3.88 | w |
| 24.42 | 3.64 | w |
| 25.08 | 3.54 | w |
| 26.10 | 3.41 | w |
| 27.12 | 3.29 | m |
| 27.86 | 3.20 | m |
| 28.26 | 3.15 | vs |

TABLE 2-continued

| 2Θ | d(Å) | I/Io % |
|---|---|---|
| 30.019 | 2.97 | m |
| 30.716 | 2.91 | w |
| 32.58 | 2.75 | w |
| 32.92 | 2.72 | w |
| 33.28 | 2.69 | m |
| 37.506 | 2.40 | w |
| 42.30 | 2.14 | w |
| 45.96 | 1.97 | w |
| 51.40 | 1.78 | w |
| 53.14 | 1.72 | w |
| 54.18 | 1.69 | w |

EXAMPLE 3

An aluminosilicate reaction solution was prepared by mixing in a container 72.77 g of aluminum sec-butoxide and 761.18 g of pentaethonium ammonium hydroxide, and 150.70 g of ethyltrimethyammonioum hydroxide (20% solution), while stirring vigorously. After thorough mixing, 215.31 g of Ludox™ AS-40 ($SiO_2$, 40%) was added. The reaction mixture was homogenized for 30 minutes, sealed in a Teflon™ bottle and placed in an oven for 18 hours at 100° C. to react the mixture and then cooled to provide an aluminosilicate solution. In one container 11.87 g of NaOH were dissolved in 100 g of deionized water and in another container 8.73 g of NaCl was dissolved in 86 g of deionized water. Both solutions were slowly added to the aluminosilicate solution and stirred for 30 minutes. The gel was placed in a 2-liter reactor and the mixture reacted at 150° C. for 140 hours. The solid product was recovered by centrifugation, washed with de-ionized water and dried at 100° C. The product was identified as UZM-29 by x-ray diffraction. Representative diffraction lines for the product are presented in Table 3. Elemental analysis showed that the UZM-29 product had a Si/Al=4.49; Na/Al=0.64, N/Al=0.32. The UZM-29 zeolite was calcined at 510° C. in air for 6 hours and was found to be crystalline after the calcination.

Scanning Electron Microscopy (SEM) showed spherical crystal aggregates that contained long prismatic crystals in each aggregate.

TABLE 3

| 2Θ | d(Å) | I/Io % |
|---|---|---|
| 10.74 | 8.23 | w |
| 12.50 | 7.07 | vs |
| 14.04 | 6.30 | w |
| 16.60 | 5.34 | s |
| 17.48 | 5.07 | m |
| 17.80 | 4.98 | w |
| 20.78 | 4.27 | w |
| 21.78 | 4.08 | s |
| 22.84 | 3.89 | m |
| 24.40 | 3.64 | w |
| 25.10 | 3.54 | w |
| 26.10 | 3.41 | w |
| 27.12 | 3.29 | m |
| 27.90 | 3.19 | m |
| 28.36 | 3.14 | s |
| 30.06 | 2.97 | m |
| 32.64 | 2.74 | w |
| 33.02 | 22.71 | w |
| 33.28 | 2.69 | m |
| 33.78 | 2.65 | w |
| 37.56 | 2.39 | w |
| 41.20 | 2.19 | w |
| 42.29 | 2.13 | w |
| 46.02 | 1.97 | w |
| 51.58 | 1.77 | w |
| 53.32 | 1.71 | w |
| 54.26 | 1.69 | w |

EXAMPLE 4

A sample of the UZM-29 prepared in Example 3 was acid washed by dissolving 42 grams of ammonium nitrate in 420 grams of de-ionized water and adding to the solution 4.2 grams of nitric acid to bring the pH to 2. The solution was heated to 80° C. and then 42 grams of UZM-29 from Example 3 were added and the slurry stirred and held at 80° C. for 2 hours. The solid was isolated by filtration and washed with one liter of de-ionized water. The final Si/Al=4.63. The product was identified as UZM-29 by x-ray diffraction. Representative diffraction lines for the acid washed product are shown in Table 4. The acid washed UZM-29 composition was calcined at 510° C. for 6 hours and was found to be slightly more crystalline then the untreated composition.

TABLE 4

| 2Θ | d(Å) | I/Io % |
|---|---|---|
| 10.86 | 8.14 | m |
| 12.66 | 6.99 | vs |
| 16.72 | 5.30 | m |
| 17.70 | 5.01 | m |
| 20.74 | 4.28 | w |
| 21.94 | 4.05 | m |
| 22.82 | 3.89 | w |
| 24.52 | 3.63 | w |
| 25.04 | 3.55 | w |
| 26.06 | 3.42 | w |
| 27.62 | 3.23 | w |
| 27.70 | 3.22 | m |
| 28.4 | 3.14 | m |
| 30.30 | 2.95 | m |
| 33.03 | 2.71 | w |
| 33.76 | 2.65 | w |
| 36.31 | 2.47 | w |
| 37.48 | 2.40 | w |
| 37.86 | 2.37 | w |
| 40.96 | 2.20 | w |
| 41.32 | 2.18 | w |
| 42.41 | 2.13 | w |
| 52.00 | 1.76 | w |
| 53.86 | 1.70 | w |
| 54.06 | 1.69 | w |

Table B Compares d-spacing for UZM-29 with examples from the literature as reported in: "A New Addition to the Phillipsite Family of Molecular Sieves: A Divalent Metal-Ion-Framework Substituted Microporous Aluminophosphate (DAF-8)", *Solid State Science* 2006, 8, 337-341 Barrett, P.A., Sankar, G., Catlow, C. R. A., Thomas, J. M., Jones, R. H., and Teat, S. J.

TABLE B

| UZM-29 | | Example 1 | | Example 2 | | Example 3 | |
|---|---|---|---|---|---|---|---|
| d(Å) | I/I₀ % | d(Å) | I/I₀ % | d(Å) | I/I₀ % | d(Å) | I/I₀ % |
| 8.2316 | w | 8.1 | w | 8.05 | w | 8.14 | w |
| 7.0744 | vs | 7.09 | s | 6.99 | m | 7.15 | vs |
| 6.3036 | w | 6.38 | w |  |  | 6.35 | w |
| 5.3353 | s | 5.35 | w | 5.33 | w | 5.38 | w |

TABLE B-continued

| UZM-29 | | Example 1 | | Example 2 | | Example 3 | |
|---|---|---|---|---|---|---|---|
| d(Å) | I/I₀ % | d(Å) | I/I₀ % | d(Å) | I/I₀ % | d(Å) | I/I₀ % |
| 5.069 | m | 5.02 | m | | | | |
| 4.9783 | w | 4.96 | m | 4.95 | m | 4.98 | m |
| 4.2716 | w | 4.29 | w | 4.24 | w | 4.25 | m |
| | | 4.11 | m | | | 4.12 | m |
| 4.0772 | s | | | 4.06 | m | 4.06 | m |
| 3.8901 | m | | | | | | |
| 3.2852 | m | 3.26 | m | | | 3.32 | m |
| 3.1954 | m | 3.19 | vs | 3.21 | m | 3.18 | vs |
| 3.1444 | s | 3.15 | m | 3.15 | vs | 3.15 | s |
| 2.9705 | m | 2.94 | m | 2.93 | w | 2.92 | w |
| 2.7409 | w | 2.75 | m | | | 2.74 | m |
| 2.7106 | w | | | 2.72 | w | 2.7 | vs |
| 2.69 | m | 2.69 | m | 2.67 | m | | |

Table B shows that UZM-29 has a different x-ray diffraction pattern to that of phillipsite.

The Thermal Stability of UZM-29

In the same paper by P. A. Barret et al cited above the authors present the X-ray absorption and X-ray diffraction spectra of Phillipsite after heating to 400° C. The X-ray diffraction spectra showed a loss in intensity of the reflections, while the absorption spectra revealed changes indicating the loss of long range order. However, it has been determined by X-ray Diffraction that UZM-29 compositions after calcination up to 510° for 6 hours in air calcination retain their crystallinity. The higher the Si/Al ratio of the UZM-29 the more stable the material, unlike phillipsite which is thermally stable only up to 400° C. Representative lines of the UZM-29 composition that was calcined at 510° C. for 6 hours are presented in Table C.

TABLE C

| 2Θ | d(Å) | I/Io % |
|---|---|---|
| 9.578 | 9.23 | w |
| 10.90 | 8.11 | w |
| 12.58 | 7.03 | vs |
| 14.02 | 6.31 | w |
| 16.68 | 5.31 | m |
| 17.84 | 4.97 | m |
| 19.74 | 4.49 | w |
| 20.74 | 4.28 | w |
| 21.86 | 4.06 | m |
| 22.78 | 3.90 | w |
| 24.50 | 3.63 | w |
| 26.12 | 3.41 | w |
| 27.64 | 3.23 | w |
| 28.36 | 3.14 | m |
| 30.44 | 2.93 | w |
| 30.88 | 2.89 | w |
| 32.98 | 2.71 | w |
| 33.66 | 2.66 | m |
| 35.39 | 2.53 | w |
| 37.54 | 2.39 | w |
| 46.38 | 1.96 | w |
| 51.96 | 1.76 | w |
| 53.64 | 1.71 | w |

The invention claimed is:
1. A hydrocarbon conversion process comprising contacting a hydrocarbon stream with a catalyst at hydrocarbon conversion conditions to give a converted product, the catalyst comprising a macroporous crystalline zeolite selected from the group consisting of UZM-29, UZM-29HS and mixtures thereof, where UZM-29 has a three-dimensional framework of at least $SiO_2$ tetrahedral units and an empirical composition in the as synthesized and anhydrous basis expressed by an empirical formula of:

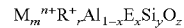

Where M is at least one exchangeable cation selected from the group consisting of alkali and alkaline earth metals, "m" is the mole ratio of M to (Al+E) and varies from greater than zero to about 2.0, R is a singly or doubly charged organoammonium cation selected from the group of pentaethonium ammonium, ethyltrimethylammonium (ETMA⁺), hexamethonium ammonium, diquat-4, pentyltrimethylammonium, choline, diethyldimethyl ammonium (DEDMA⁺), trimethylpropylammonium, dimethyldiethanolammonium, tetraethyl ammonium (TEA⁺), tetrapropylammonium (TPA⁺), dimethylhexylamine, diethanolamine, and mixtures thereof, "r" is the mole ratio of R to (Al+E) and has a value of about 0.25 to about 2.0, "n" is the weighted average valence of M and has a value of about 1 to about 3, E is an element selected from the group consisting of gallium, iron, boron, and mixtures thereof, "x" is the mole fraction of E and has a value from 0 to about 1.0, "y" is the mole ratio of Si to (Al+E) and varies from greater than 2 to about 10 and "z" is the mole ratio of O to (Al+E) and has a value determined by the equation:

$$z = (m \cdot n + p \cdot r + 3 + 4 \cdot y)/2$$

And is characterized in that it has the x-ray diffraction pattern having at least the d-spacings and intensities set forth in Table A:

TABLE A

| 2Θ | d(Å) | I/Io % |
|---|---|---|
| 10.74-10.86 | 8.14-8.23 | w-m |
| 12.50-12.6 | 6.99-7.07 | vs |
| 16.60-16.72 | 5.30-5.33 | s-vs |
| 17.48-17.7 | 5.01-5.07 | m |
| 17.80-17.88 | 4.96-4.98 | w |
| 20.74-20.81 | 4.26-4.28 | w |
| 21.74-21.94 | 4.05-4.08 | m-s |
| 22.82-22.88 | 3.88-3.89 | w-m |
| 24.40-24.52 | 3.62-3.64 | w |
| 25.08-25.10 | 3.54-3.55 | w |
| 26.06-26.1 | 3.41-3.42 | w-m |
| 27.10-27.12 | 3.28-3.29 | m |
| 27.70-27.90 | 3.20-3.22 | m |
| 28.26-28.44 | 3.14-3.15 | s-vs |
| 30.00-30.30 | 2.94-2.97 | m |
| 32.58-32.64 | 2.74-2.75 | w |
| 33.02-33.03 | 2.71-2.71 | w |
| 33.28-33.29 | 2.69-2.70 | m |
| 33.76-33.82 | 2.65-2.65 | w |
| 37.481-37.56 | 2.39-2.40 | w |
| 41.202-42.41 | 2.13-2.19 | w |
| 45.96-46.01 | 1.97-1.98 | w |
| 51.4-52.00 | 1.70-1.77 | w |
| 54.05-54.26 | 1.69-1.70 | w | and is thermally stable up to a temperature of at least 400° C.; and UZM-29HS has a three-dimensional framework of at least $SiO_2$ tetrahedral units and an empirical composition on an anhydrous basis of:

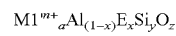

Where M1 is at least one exchangeable cation selected from the group consisting of alkali and alkaline earth metals, rare earth metals, ammonium ion, hydrogen ion and mixtures thereof, "a" is the mole ratio of M1 to (Al+E) and varies from about 0.05 to about 50, "n" is the weighted average valence of M1 and had a value of about +1 to about +3, E is an element selected from the group consisting of gallium, iron, boron and mixtures thereof, "x" is the mole fraction of E and varies from 0 to 1.0, y' is the mole ratio of Si to (Al+E) and varies from greater than about 4 to virtually pure silica and z' is the mole ratio of O to (Al+E) and has a value determined by the equation:

$$z'=(a\cdot n+3+4\cdot y')/2$$

the zeolite characterized in that it has an x-ray diffraction pattern having at least the d=spacings and relative intensities set forth in Table C:

TABLE C

| 2Θ | d(Å) | I/Io % |
|---|---|---|
| 10.86 | 8.14 | m |
| 12.66 | 6.99 | vs |
| 16.72 | 5.30 | m |
| 17.70 | 5.01 | m |
| 20.74 | 4.28 | w |
| 21.94 | 4.05 | m |
| 22.82 | 3.89 | w |
| 24.52 | 3.63 | w |
| 25.04 | 3.55 | w |
| 26.06 | 3.42 | w |
| 27.62 | 3.23 | w |

TABLE C-continued

| 2Θ | d(Å) | I/Io % |
|---|---|---|
| 27.70 | 3.22 | m |
| 28.44 | 3.14 | m |
| 30.30 | 2.95 | m |
| 33.03 | 2.71 | w |
| 33.76 | 2.65 | w |
| 36.31 | 2.47 | w |
| 37.48 | 2.40 | w |
| 37.86 | 2.37 | w |
| 40.96 | 2.20 | w |
| 41.33 | 2.18 | w |
| 42.41 | 2.13 | w |
| 52.00 | 1.76 | w |
| 53.86 | 1.70 | w |
| 54.06 | 1.69 | w |

And is thermally stable up to a temperature of at least 400° C.

2. The process of claim 1 where "x" is zero.

3. The process of claim 1 where R is pentaethonium ammonium and ethyltrimethylammonium.

4. The process selected from the group consisting of isomerization of butane, alkylation, and conversion on oxygenates to olefins of claim 1 where R is pentaethonium ammonium, ethyltrimethylammonium and M is sodium.

* * * * *